(12) United States Patent
Park et al.

(10) Patent No.: US 12,128,247 B2
(45) Date of Patent: Oct. 29, 2024

(54) SKIN CARE DEVICE

(71) Applicant: AMOSENSE CO., LTD., Cheonan-si (KR)

(72) Inventors: Jin Pyo Park, Cheonan-si (KR); Jun Ho Park, Cheonan-si (KR); Sang Dong Jeong, Cheonan-si (KR)

(73) Assignee: AMOSENSE CO., LTD., Cheonan-si (KR)

(*) Notice: Subject to any disclaimer, the term of this patent is extended or adjusted under 35 U.S.C. 154(b) by 431 days.

(21) Appl. No.: 17/604,825

(22) PCT Filed: Mar. 23, 2020

(86) PCT No.: PCT/KR2020/003930
§ 371 (c)(1),
(2) Date: Oct. 19, 2021

(87) PCT Pub. No.: WO2020/218745
PCT Pub. Date: Oct. 29, 2020

(65) Prior Publication Data
US 2022/0203116 A1 Jun. 30, 2022

(30) Foreign Application Priority Data

Apr. 25, 2019 (KR) ........................ 10-2019-0048467
Mar. 20, 2020 (KR) ........................ 10-2020-0034459

(51) Int. Cl.
*A61N 5/06* (2006.01)
(52) U.S. Cl.
CPC .... *A61N 5/0616* (2013.01); *A61N 2005/0626* (2013.01)
(58) Field of Classification Search
None
See application file for complete search history.

(56) References Cited

U.S. PATENT DOCUMENTS

2015/0230863 A1\* 8/2015 Youngquist .......... A61B 18/203
606/9
2019/0175907 A1 6/2019 You et al.
(Continued)

FOREIGN PATENT DOCUMENTS

CN 109069853 A 12/2018
CN 109152925 A 1/2019
(Continued)

OTHER PUBLICATIONS

International Search Report cited in PCT/KR2020/003930 dated Jul. 8, 2020, 2 pages.

*Primary Examiner* — Sana Sahand
(74) *Attorney, Agent, or Firm* — ROTHWELL, PIGG, ERNST & MANBECK, P.C.

(57) ABSTRACT

A skin care device is provided. A skin care device according to an exemplary embodiment of the present invention comprises: a body including a first surface having a predetermined area; two contact terminals disposed to be spaced apart from each other on the first surface, and when electric power is applied thereto, generating a potential difference on a users skin to change an electrical environment of the users skin; two sensing terminals disposed to be spaced apart from each other on the first surface and sensing oil and moisture of the users skin when electric power is applied thereto; a plurality of light sources mounted on a circuit board disposed inside the body, such that the light sources are located behind the first surface, the light sources emitting light beams having different wavelength bands; and a control unit for controlling the entire operation.

13 Claims, 8 Drawing Sheets

(56) References Cited

U.S. PATENT DOCUMENTS

2020/0046999 A1  2/2020  Lim et al.
2020/0121941 A1  4/2020  Kwon et al.

FOREIGN PATENT DOCUMENTS

| JP | 2019013689 A | 1/2019 | |
|----|----|----|----|
| KR | 100787874 B1 | 12/2007 | |
| KR | 10-2012-0128427 A | 11/2012 | |
| KR | 20140039459 A | 4/2014 | |
| KR | 20170103597 A | 9/2017 | |
| WO | WO-2017213442 A1 * | 12/2017 | ............ A61B 5/442 |
| WO | 2018066778 A1 | 4/2018 | |

* cited by examiner

SKIN CARE DEVICE

CROSS REFERENCE TO RELATED APPLICATIONS

This application is a 35 U.S.C. 371 National Phase Entry Application from PCT/KR2020/003930, filed Mar. 23, 2020, which claims the benefit of Korean Patent Application Nos. 10-2019-0048467 filed on Apr. 25, 2019 and 10-2020-0034459 filed on Mar. 20, 2020, the disclosures of which are incorporated herein in their entirety by reference.

TECHNICAL FIELD

The present invention relates to a skin care device.

BACKGROUND

In general, skin care devices are broadly classified into skin care devices that transmit ultrasonic waves to the user's skin and skin care devices that apply an electric current.

That is, skin care devices using ultrasonic waves use a method of physically tapping the skin, and skin care devices that apply an electric current use a method that ionizes sebum, wastes and the like by applying an electric current to the user's skin and removes the same from the skin or allows skin nutrients to be absorbed deeply into the skin.

Such skin care devices can exhibit an optimal effect only when appropriately used according to the user's skin condition. For example, if appropriate electrical stimulation is applied according to the user's skin moisture and oil conditions, the skin improvement effect can be increased. However, if electrical stimulation which is inappropriate for the moisture and oil conditions of the user's skin is applied, the user's skin may be damaged.

Meanwhile, the moisture and oil conditions of the user's skin change every moment according to time or environment. Accordingly, the user needs to accurately diagnose the current skin condition before using a skin care device.

However, there is a problem in that conventional skin care devices can only apply electrical stimulation and cannot diagnose a user's current skin condition when used.

SUMMARY OF THE INVENTION

The present invention is directed to provide a skin care device capable of diagnosing a user's skin condition and performing skin care suitable for the diagnosed skin condition.

One aspect of the present invention provides a skin care device, including a body including a first surface having a predetermined area; two contact terminals disposed to be spaced apart from each other on the first surface, and when electric power is applied thereto, generating a potential difference on a user's skin to change an electrical environment of the user's skin; two sensing terminals disposed to be spaced apart from each other on the first surface and sensing oil and moisture of the user's skin when electric power is applied thereto; a plurality of light sources mounted on a circuit board disposed inside the body, the circuit board being located behind the first surface, the light sources emitting light beams having different wavelength bands; and a control unit for controlling the entire operation.

In addition, the two contact terminals and the two sensing terminals may be disposed in an annular shape along the periphery of an edge side of the first surface, and the two sensing terminals may be disposed to be located between the two contact terminals.

In addition, the first surface may be formed as an inclined, and the first surface may be an upper surface of the body.

In addition, the two sensing terminals may be disposed to be located on the upper end side of the inclined surface.

In addition, a contact surface of the sensing terminal in contact with the user's skin may be formed to have a relatively narrower area than a contact surface of the contact terminal in contact with the user's skin.

In addition, the first surface may include a light-transmitting member integrally formed inside to emit light beams generated by the light source to the outside.

In addition, the skin care device may further include a proximity sensor mounted on the circuit board.

In addition, the proximity sensor may be disposed to be located at a position relatively closer to the two sensing terminals than the plurality of light sources.

In this case, the control unit may change the light source to a light-off state, when the two contact terminals are not in contact with the user's skin in a state in which the light source is turned on, and the spacing distance from the user's skin measured through the proximity sensor is more than a preset distance.

Moreover, the control unit may maintain a light-on state of the light source, when the two contact terminals are not in contact with the user's skin in a state in which the light source is turned on, and the spacing distance from the user's skin measured through the proximity sensor is within a preset distance.

In addition, the two contact terminals and the two sensing terminals may be in contact with a plurality of elastic terminals mounted on the circuit board to be electrically connected to the circuit board.

In addition, the skin care device may further include a plurality of indicator LEDs embedded on the body to emit light beams according to the user's oil and moisture condition information measured through the two sensing terminals.

In addition, the body may be formed to have a relatively wider width from the top to the bottom.

In addition, the body may include a case having an inner space with an open upper part and an annular connecting member integrally formed on the open upper edge side of the case, and the two contact terminals and the two sensing terminals may be integrally formed with the connecting member.

According to the present invention, after a user accurately diagnoses the skin condition for oil and moisture in the skin through one device, the device can be operated in a mode suitable for the diagnosed skin condition. Through this, the user can manage his or her own skin in an optimal state.

DETAILED DESCRIPTION OF THE INVENTION

Hereinafter, embodiments of the present invention will be described in detail with reference to the accompanying drawings so that those skilled in the art to which the present invention pertains may easily implement the present invention. The present invention may be implemented in various different forms and is not limited to the embodiments described herein. In the drawings, parts irrelevant to the description are omitted in order to clearly describe the present invention, and the same or similar reference numerals are assigned to the same or similar components throughout the specification.

Figure 1:
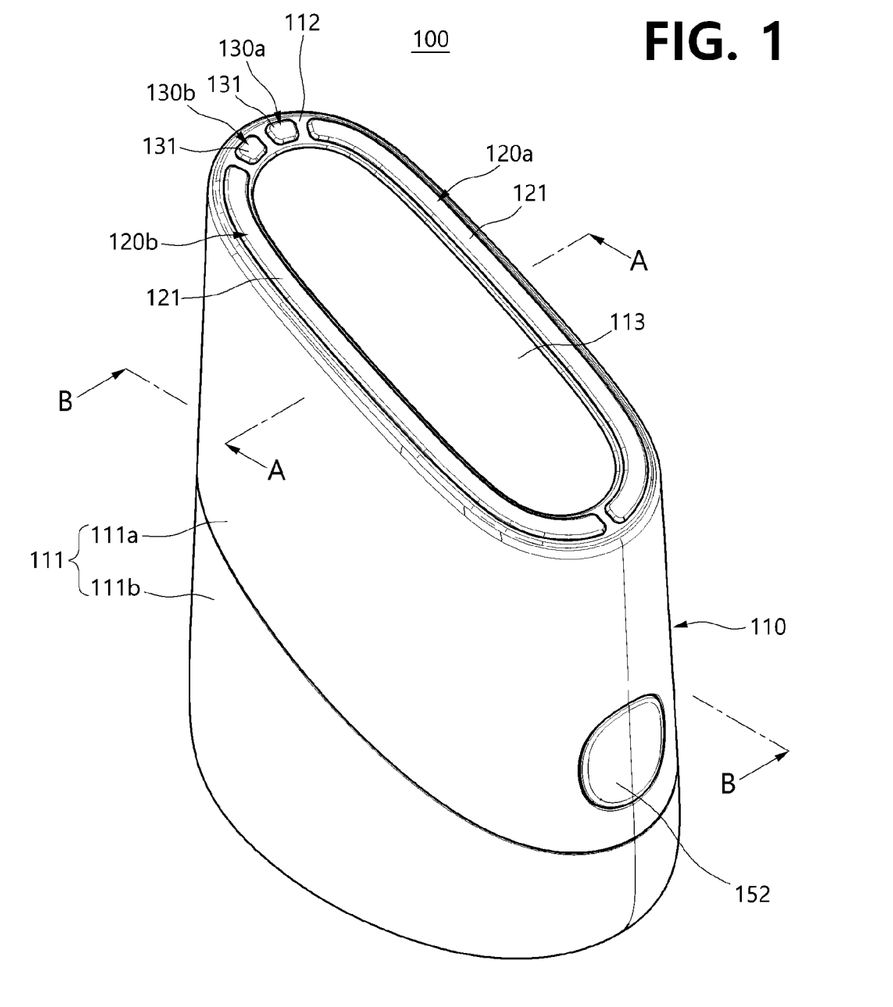
FIG. 1 is a view showing a skin care device according to one embodiment of the present invention.
Figure 2:
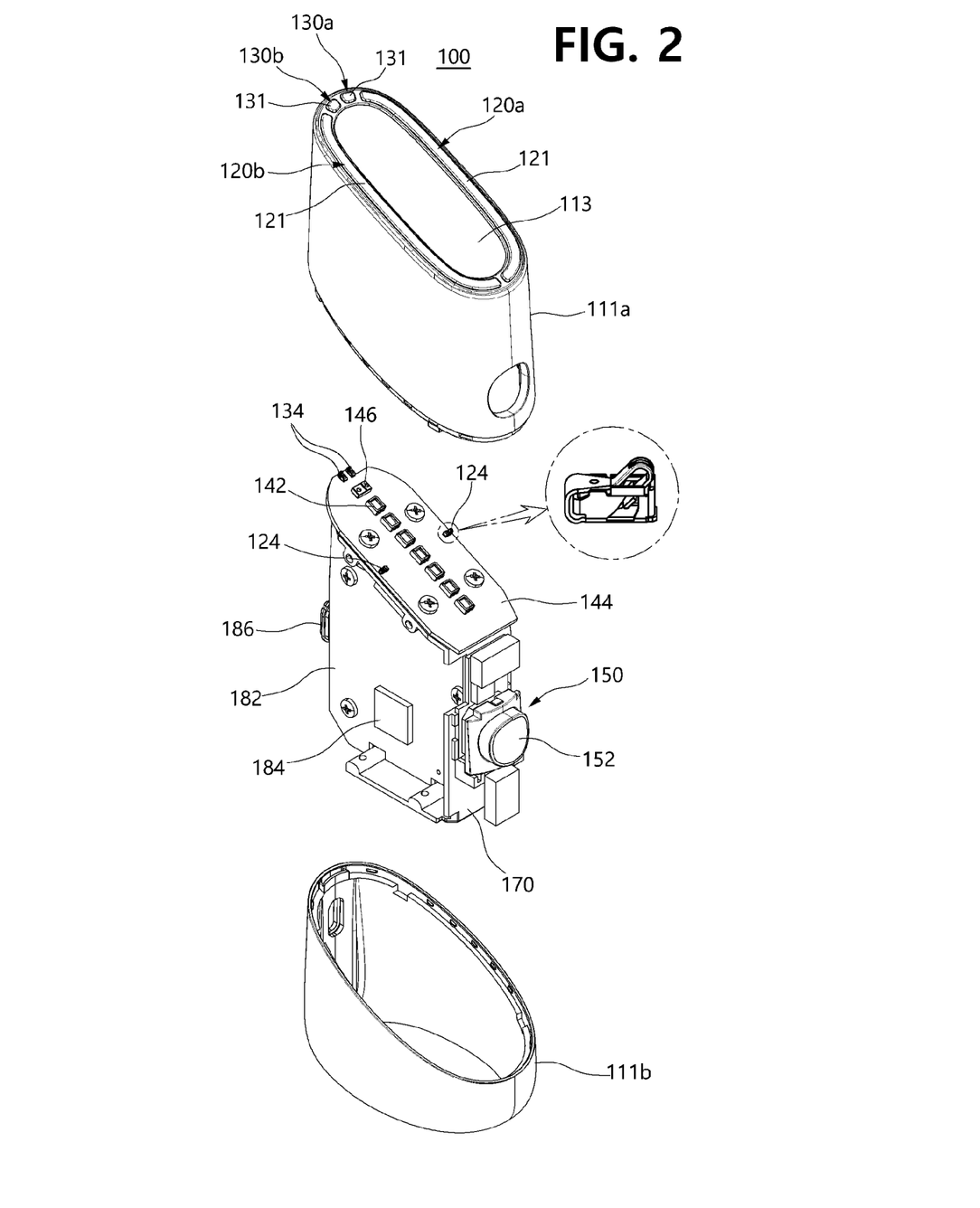
FIG. 2 is an exploded view of FIG. 1.

As illustrated in FIGS. 1 and 2, the skin care device 100 according to one embodiment of the present invention includes a body 110, two contact terminals 120*a* and 120*b*, two sensing terminals 130*a* and 130*b*, a plurality of light sources 142 and a control unit.

The body 110 has an overall external appearance, and various components such as a light source 142, circuit boards 144, 154 and 182, a battery 160 and the like may be accommodated therein.

To this end, the body 110 may include a case 111 having an internal space.

For example, the case 111 may include an upper case 111*a* with an open lower portion and a lower case 111*b* with an open upper portion, and a lower portion side of the upper case 111*a* may be detachably coupled with an upper portion side of the lower case 111*b*.

In this case, the body 110 may include a first surface having a predetermined area, and the first surface may be an arrangement surface on which the two contact terminals 120*a* and 120*b* and two sensing terminals 130*a* and 130*b* are disposed.

For example, the first surface may be an upper surface of the body 110, the upper surface of the body 110 may be an upper surface of the case 111, and the upper surface of the case 111, on which the first surface is formed, may be the upper surface of the upper case 111*a*.

In this case, in the skin care device 100 according to one embodiment of the present invention, the two contact terminals 120*a* and 120*b* and the two sensing terminals 130*a* and 130*b* may be disposed on the first surface as described above. In addition, the two contact terminals 120*a* and 120*b* and the two sensing terminals 130*a* and 130*b* may protrude from the first surface to a predetermined height.

For this reason, when the user contacts the first surface towards the skin, the contact areas of the two contact terminals 120*a* and 120*b* and the two sensing terminals 130*a* and 130*b* on the user's skin may increase.

In addition, the first surface may be formed as an inclined surface having a predetermined inclination.

As a non-limiting example, the inclined surface may be formed such that the right side has a relatively lower height than the left side with respect to the bottom surface of the case 111 based on the drawing of FIG. 1.

In this case, the two contact terminals 120*a* and 120*b* and the two sensing terminals 130*a* and 130*b* disposed on the inclined surface may be disposed on the inclined surface, and the two contact terminals 120*a* and 120*b* and the two sensing terminals 130*a* and 130*b* may protrude at a predetermined height from the inclined surface.

Accordingly, the two contact terminals 120*a* and 120*b* and the two sensing terminals 130*a* and 130*b* disposed on the inclined surface may be disposed to have a predetermined inclination with respect to the horizontal surface.

For this reason, even if the user does not excessively bend the wrist while holding a part of the body 110, when the inclined surface is moved towards the user's skin, the two contact terminals 120*a* and 120*b* and the two sensing terminals 130*a* and 130*b* may smoothly contact the user's skin.

In this case, the body 110 may include a light-transmitting member 113 such that light beams generated from the light source 142 may be emitted from the inside of the body 110 to the outside, and the light-transmitting member 113 may be disposed to be located inside the first surface.

To this end, in addition to the case 111 described above, the body 110 may include an annular connecting member 112 integrally formed with the case 111 and a light-transmitting member 113 integrally formed with the annular connecting member 112.

For example, the case 111 may have an open upper portion of the upper case 111*a*, and the annular connecting member 112 may be integrally formed on the open upper edge side of the upper case 111*a*. In addition, the light-transmitting member 113 may have an edge side formed integrally with the connecting member 112.

Moreover, the two contact terminals 120*a* and 120*b* and the two sensing terminals 130*a* and 130*b* may be disposed along the connecting member 112, and the two contact terminals 120*a* and 120*b* and the two sensing terminals 130*a* and 130*b* may be integrally formed with the connecting member 112.

As a non-limiting example, the upper case 111*a*, the connecting member 112, the two contact terminals 120*a* and 120*b*, the two sensing terminals 130*a* and 130*b* and the light-transmitting member 113 may be integrated through insert molding.

Figure 5:
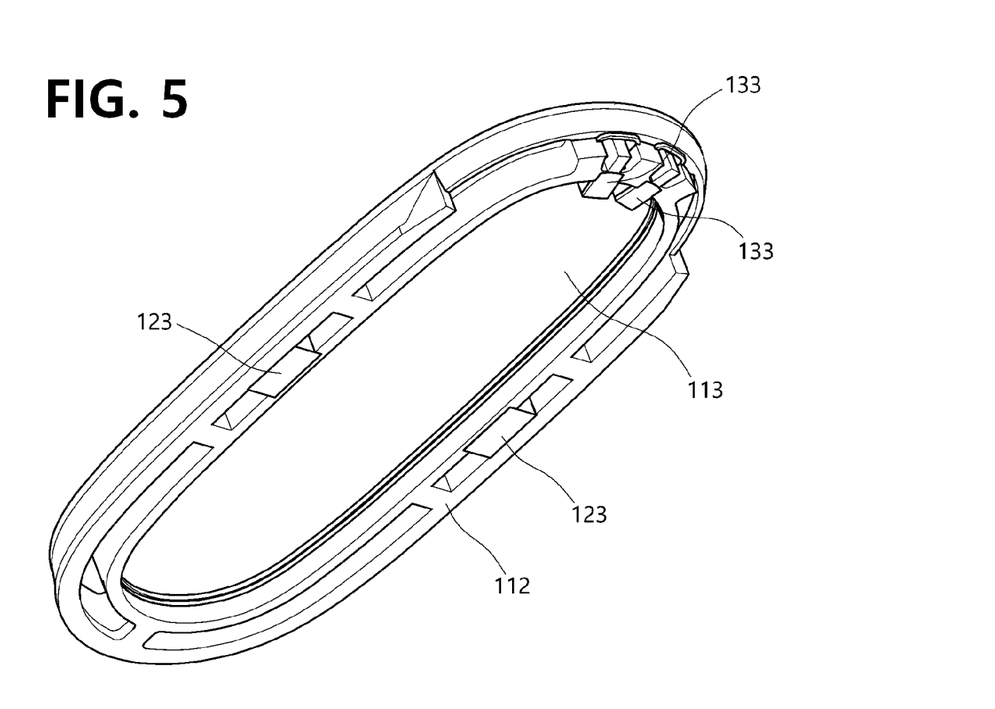
FIG. 5 is a view showing a state in which a connecting member, a light-transmitting member, a contact terminal and a sensing terminal that are forcibly separated from the case of FIG. 1 are combined.

That is, as illustrated in FIG. 5, while physically separated from each other, the two contact terminals 120*a* and 120*b*, the two sensing terminals 130*a* and 130*b* and the light-transmitting member 113 may be integrated with each other through primary insert molding to form the connecting member 112.

In addition, when the upper case 111*a* is formed through secondary insert molding in a state in which the two contact terminals 120*a* and 120*b*, the two sensing terminals 130*a* and 130*b* and the light-transmitting member 113 are integrated through the connecting member 112, the connecting member 112 and the upper case 111*a* may be integrated with each other in a state in which the two contact terminals 120*a* and 120*b* and the two sensing terminals 130*a* and 130*b* are fixed to the connecting member 112.

Accordingly, in the skin care device 100 according to one embodiment of the present invention, the upper surface of the connecting member 112 may form a first surface of the body 110, and the two contact terminals 120*a* and 120*b* and the two sensing terminals 130*a* and 130*b*, which are integrally formed with the connecting member 112, may be arranged in an annular shape along the connecting member 112 forming the first surface.

Through this, the two contact terminals 120*a* and 120*b* and the two sensing terminals 130*a* and 130*b* may be disposed in an annular shape along the periphery of an edge side of the first surface, and the light-transmitting member 113 may be disposed to be located inside the connecting member 112.

For this reason, in the skin care device 100 according to one embodiment of the present invention, when the user contacts the first surface towards the skin, the two contact terminals 120a and 120b and the two sensing terminals 130a and 130b may be in direct contact with the user's skin, and light beams emitted to the outside through the light-transmitting member 113 may be irradiated towards the user's skin.

In addition, in the skin care device 100 according to one embodiment of the present invention, in a state in which the two contact terminals 120a and 120b and the two sensing terminals 130a and 130b are integrated with the connecting member 112 through primary insert molding, the connecting member 112 and the upper case 111a are integrated through secondary insert molding such that the two contact terminals 120a and 120b and the two sensing terminals 130a and 130b may be disposed in an annular arrangement along the edge of the first surface.

Moreover, in the skin care device 100 according to one embodiment of the present invention, since the two contact terminals 120a and 120b, the two sensing terminals 130a and 130b, the light-transmitting member 113, the connecting member 112 and the upper case 111a are integrally formed, all parts may be easily assembled when a frame unit 170 to which various parts are fastened is inserted into either the upper case 111a or the lower case 111b, and then the upper case 111a and the lower case 111b are combined with each other.

Meanwhile, the skin care device 100 according to one embodiment of the present invention may have an overall shape having a narrow upper portion and a wide lower portion.

Figure 3:
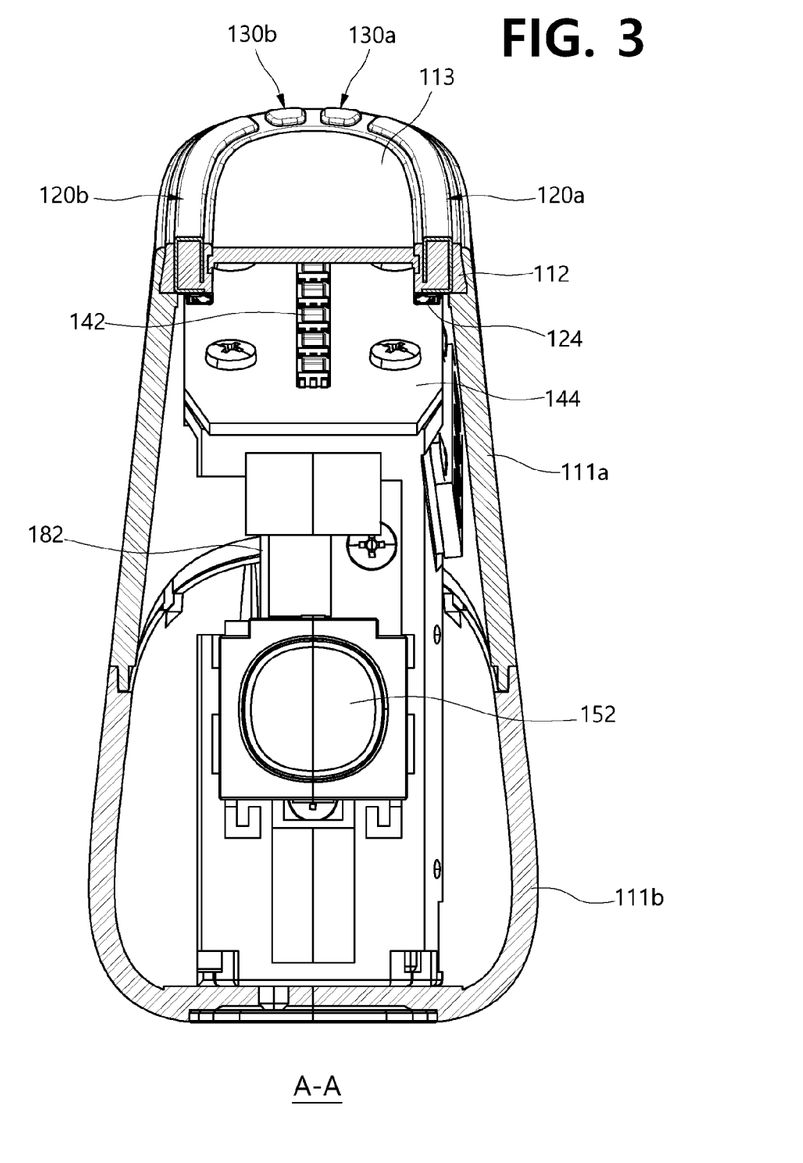
FIG. 3 is a view showing a state viewed from the A-A direction by cutting a part of the case in FIG. 1.

For example, the body 110 may be formed to have a relatively wider width from top to bottom as illustrated in FIG. 3.

Through this, when the user grips the lower portion side of the body 110 having a relatively wider width, the user may increase a sense of grip and may stably grip the body 110.

For this reason, when the skin care device 100 according to one embodiment of the present invention treats a highly curved body part such as the face, it is possible to prevent the skin care device 100 from being separated from the user's hand, even if the user rubs the highly curved body part such as the face.

When electric power is applied to the two contact terminals 120a and 120b, a potential difference may be generated on the user's skin, thereby changing the electrical environment of the user's skin. Through this, the two contact terminals 120a and 120b may increase skin penetration of ionic drugs.

That is, the two contact terminals 120a and 120b may implement a known iontophoresis function. Through this, the skin care device 100 according to one embodiment of the present invention may apply a direct current towards the user's body using electric power supplied from a battery 160 when electric power is applied in a state in which the two contact terminals 120a and 120b are in contact with the user's skin, and the user's skin and the two contact terminals 120a and 120b may form a closed circuit to move ions.

Moreover, when electric power is applied, a voltage drop may occur between the two contact terminals 120a and 120b due to the user's skin resistance. Through this, the control unit may determine whether the two contact terminals 120a and 120b are in contact with the user's skin.

To this end, the two contact terminals 120a and 120b may be spaced apart on the first surface of the body 110 as described above. That is, in the skin care device 100 according to one embodiment of the present invention, the two contact terminals 120a and 120b for the iontophoresis function may be implemented in a bi-polar manner in which these are respectively fixed on the first surface, which is the same surface, while being spaced apart from each other.

Accordingly, when the user contacts the first surface towards a body part in a state in which the user applies cosmetics to the body part to be treated, the two contact terminals 120a and 120b, which are spaced apart on the same surface, may contact the body part at the same time.

In this case, as illustrated in FIG. 1, the two contact terminals 120a and 120b may include a first skin contact surface 121 having a predetermined area. Through this, the two contact terminals 120a and 120b may be in contact with the user's skin over a large area through the first skin contact surface 121.

Figure 6:
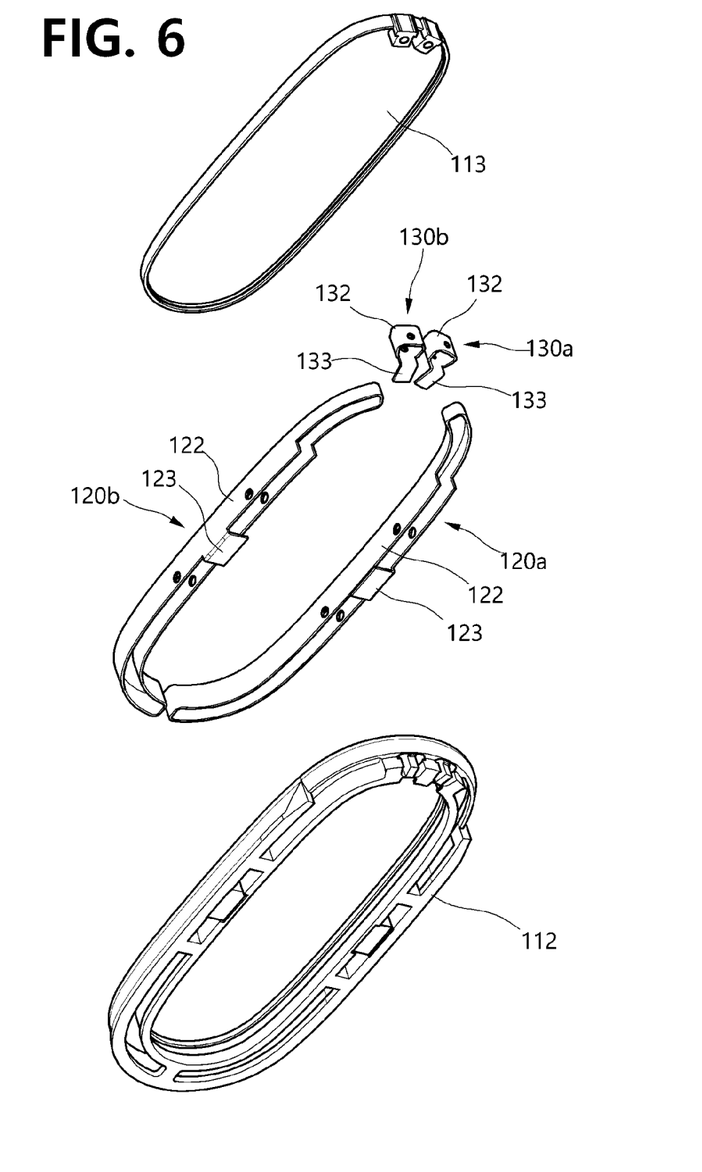
FIG. 6 is a view forcibly separating the connecting member, the light-transmitting member, the contact terminal and the sensing terminal in FIG. 5.

In addition, as illustrated in FIG. 6, the two contact terminals 120a and 120b may respectively include a first extension part 122 extending a predetermined length downward from the edge of the first skin contact surface 121. Through this, in a case in which the two contact terminals 120a and 120b are integrated with the connecting member 112 through insert molding, these may be firmly fixed to the connecting member 112 side through the first extension part 122.

Moreover, the two contact terminals 120a and 120b may respectively include a plate-shaped first terminal contact surface 123 that is bent in one direction from the end of the first extension portion 122, and as illustrated in FIG. 5, the plate-shaped first terminal contact surface 123 may be disposed in the connecting member 112 so as to be exposed to the outside.

As such, the first terminal contact surface 123 may directly contact an elastic terminal 124 mounted on a circuit board 144. Through this, the two contact terminals 120a and 120b may be electrically connected to the circuit board 144 respectively through the first terminal contact surfaces 123 in contact with the elastic terminal 124, and electric power supplied from the battery 160 may be applied to the two contact terminals 120a and 120b through the circuit board 144.

Herein, the elastic terminal 124 may be made of a material having electrical conductivity and elasticity, and at least part thereof may be elastically deformed.

The two sensing terminals 130a and 130b may sense oil and moisture of the users skin when electric power is applied. That is, when electric power is applied in a state in which the two sensing terminals 130a and 130b are in contact with the users skin, the two sensing terminals 130a and 130b may generate electrical signals according to the moisture and oil of the users skin.

In this case, the control unit may include a moisture and oil measurement program code.

Through this, in the skin care device 100 according to one embodiment of the present invention, when an electrical signal is input to the control unit through the two sensing terminals 130a and 130b, the control unit may determine the current condition of the users skin based on the previously input comparison values.

To this end, the two sensing terminals 130a and 130b may be spaced apart on the first surface of the body 110 as described above. Accordingly, when the user contacts the first surface towards a body part in a state in which the user applies cosmetics to the body part to be treated, the two sensing terminals 130a and 130b spaced apart on the same surface may be simultaneously in contact with the body part.

In this case, as illustrated in FIG. 1, the two sensing terminals 130a and 130b may include a second skin contact surface 131 having a predetermined area, and the second skin contact surface 131 may have a relatively narrower area than the first skin contact surface 121 of the contact terminals 120a and 120b.

Moreover, the two sensing terminals 130a and 130b may be disposed on the first surface so as to be located between the two contact terminals 120a and 120b, and in a case in which the first surface is formed as an inclined surface having a predetermined inclination, the two sensing terminals 130a and 130b may be disposed to be located on the upper end portion of the inclined surface.

Herein, the upper end portion of the inclined surface may be a portion having a relatively large height difference from the bottom surface of the case 111 among both ends.

Accordingly, in the skin care device 100 according to one embodiment of the present invention, the two sensing terminals 130a and 130b for measuring moisture and oil of the user's skin may also be easily contacted directly with a curved face portions and a narrow area. Through this, the two sensing terminals 130a and 130b may easily measure oil and moisture of the curved portions of the skin, and since these are formed in a narrow area, the accuracy of the measurement may be improved.

In this case, the skin care device 100 according to one embodiment of the present invention may generate a notification corresponding to the current condition of the user's skin measured through the two sensing terminals 130a and 130b.

For example, a notification corresponding to the current condition of the user's skin may be output through lighting of the LED.

Figure 7:
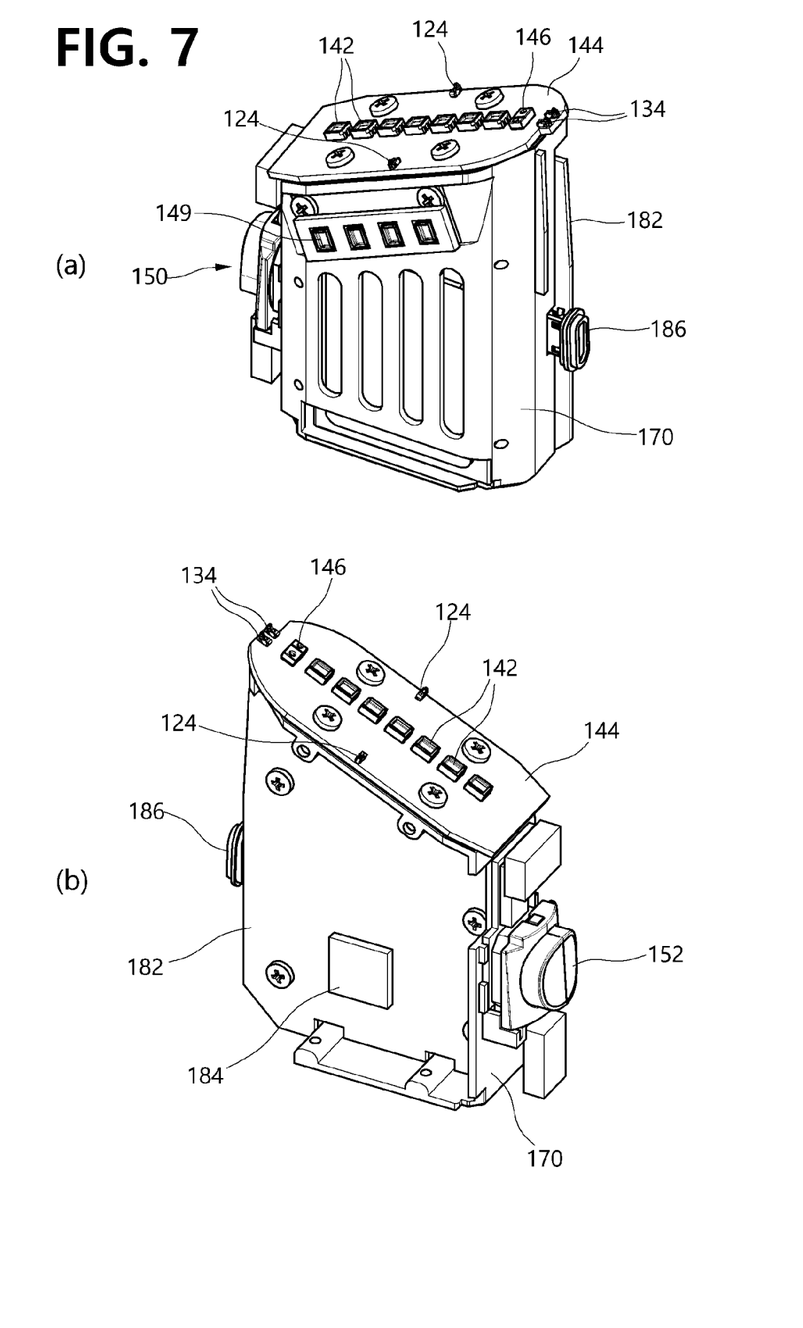
FIG. 7 is a view showing a configuration built into the body in FIG. 1.

To this end, as illustrated in (a) of FIG. 7, the skin care device 100 according to one embodiment of the present invention may include a plurality of indicator LEDs 149, and the plurality of indicator LEDs 149 may be embedded inside the body 110, and light beams emitted from the plurality of indicator LEDs 149 may be emitted to the outside through the case 111.

Through this, in the skin care device 100 according to one embodiment of the present invention, when an electrical signal is input to the control unit through the two sensing terminals 130a and 130b, the control unit may determine the current condition of the user's skin based on the previously input comparison values, and a result of the current condition of the user's skin determined by the control unit may be output to the indicator LEDs 149 through the control of the control unit.

In this case, the information on the current condition of the skin output through the indicator LEDs 149 may be identified through the total number of the indicator LEDs 149 that are lit, or it may also be identified through the color of the light beams output from the indicator LEDs 149.

Herein, the information output through the indicator LEDs 149 may be utilized as information recommending an operation mode suitable for the current condition of the user's skin. Moreover, the number of indicator LEDs 149 which are lit according to changes in the moisture and oil contents of the user's skin during skin care may be changed, or the output color may be changed.

For this reason, the user may diagnose the current condition of the body part to be treated through the two sensing terminals 130a and 130b, and then appropriately select the operation mode of the device according to the diagnosed current condition.

Meanwhile, as illustrated in FIG. 6, the two sensing terminals 130a and 130b may respectively include a second extension part 132 extending a predetermined length downward from the edge of the second skin contact surface 131. Through this, in a case in which the two sensing terminals 130a and 130b are integrated with the connecting member 112 through insert molding, the two sensing terminals 130a and 130b will be firmly fixed towards the connecting member 112 through the second extension part 132.

Moreover, the two sensing terminals 130a and 130b may respectively include a plate-shaped second terminal contact surface 133 which is bent in one direction from the end of the second extension part 132, and the plate-shaped second terminal contact surface 133 may be disposed on the connecting member 112 to be exposed to the outside as illustrated in FIG. 5.

Similar to the first terminal contact surface 123 described above, the second terminal contact surface 133 may directly contact the elastic terminal 134 mounted on the circuit board 144. Through this, the two sensing terminals 130a and 130b may be electrically connected to the circuit board 144 respectively through the second terminal contact surface 133 in contact with the elastic terminal 134, and electric power supplied from the battery 160 may be applied to the two sensing terminals 130a and 130b through the circuit board 144.

The plurality of light sources 142 may generate light beams having a predetermined wavelength band when electric power is applied. Through this, the user may obtain a beneficial effect according to the wavelength of light beams by supplying the light beams generated from the plurality of light sources 142 to the skin in need of care.

In this case, the skin care device 100 according to one embodiment of the present invention may be provided such that the plurality of light sources 142 may irradiate light beams having different wavelength bands.

Through this, the skin care device 100 according to one embodiment of the present invention may have a variety of wavelength bands of light beams generated from the plurality of light sources 142 such that various effects such as the soothing effect of skin, improvement of skin texture, soothing care of sensitive skin, skin contour improvement, skin elasticity improvement, skin elasticity restoration, skin lifting improvement, skin gloss improvement and the like may be obtained thereby through one device.

For example, the plurality of light sources 142 may be operated in a first operation mode for irradiating light at a wavelength band of 400 to 480 nm, a second operation mode for irradiating light at a wavelength band of 550 to 610 nm and a third operating mode for irradiating light at a wavelength band of 610 to 650 nm.

Moreover, the plurality of light sources 142 may be operated in a fourth operation mode in which the first operation mode, the second operation mode and the third operation mode are sequentially operated. In this case, the skin care device 100 according to one embodiment of the present invention may also vary the intensity of the current applied to the user's skin through the two contact terminals 120a and 120b according to the above-described operation modes.

However, the wavelength band of light beams generated from the plurality of light sources 142 is not limited thereto, and it may be appropriately changed as long as it is a wavelength band capable of generating beneficial effects on the user's skin.

Figure 4:
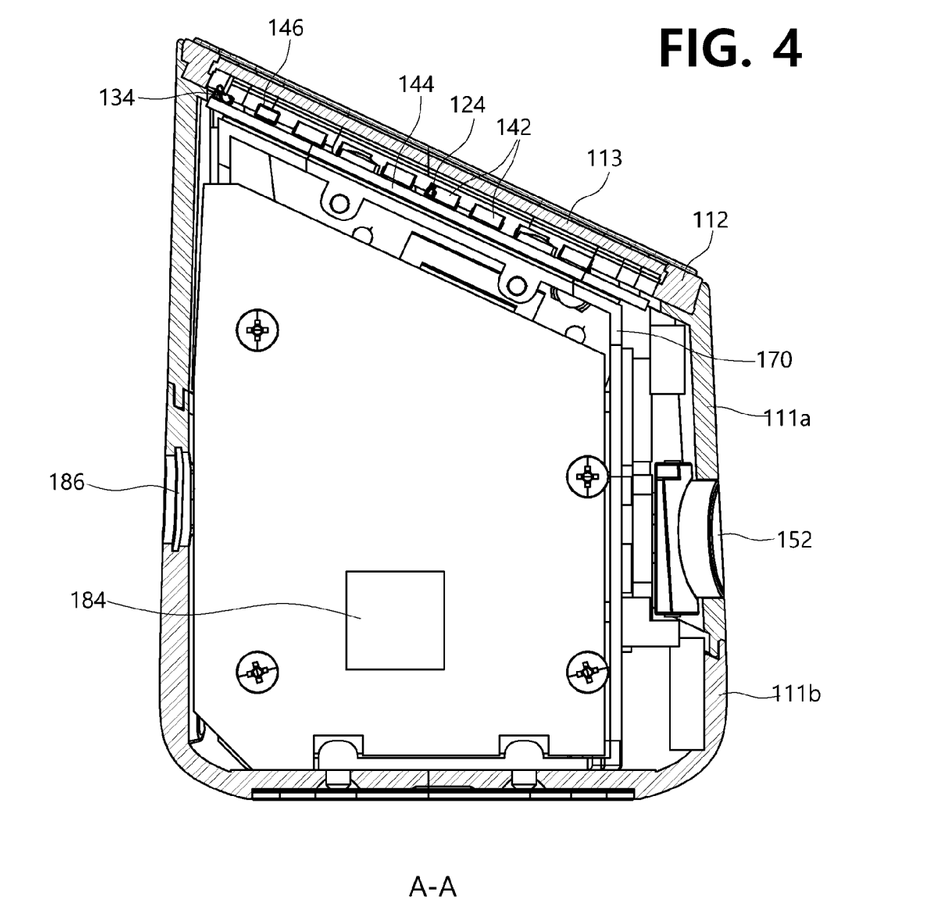
FIG. 4 is a view showing a state viewed from the B-B direction by cutting a part of the case in FIG. 1.

Such a plurality of light sources 142 may be mounted on a circuit board 144 disposed inside the body 110 as illustrated in FIGS. 3 and 4, and the circuit board 144 may be disposed to be located at a position corresponding to the light-transmitting member 113 inside the body 110.

Through this, the plurality of light sources 142 mounted on the circuit board 144 may be spaced apart from each other by the same distance with the light-transmitting member 113, respectively.

Herein, the elastic terminals 124 and 134 may be respectively mounted on the side of the circuit board 144 so as to be located at positions corresponding to the two contact terminals 120a and 120b and the two sensing terminals 130a and 130b.

Moreover, in a case in which the first surface is formed as an inclined surface having a predetermined inclination, the circuit board 144 may be disposed to be inclined at the same angle as the inclined surface inside the body 110. Through this, even if the first surface is formed as an inclined surface, each of the plurality of light sources 142 mounted on the circuit board 144 may be spaced apart from each other by the same distance with the light-transmitting member 113.

In this case, the plurality of operation modes may be achieved through manipulation of a button unit 150 provided on one side of the body 110.

To this end, as illustrated in FIGS. 1 and 2, the button unit 150 may include at least one button 152 exposed to the outside on one side of the body 110 and a circuit board 154 disposed inside the body and having a circuit part for generating a signal corresponding to the manipulation of the button 152, and the circuit board 154 may be electrically connected to a main circuit board 182 constituting the control unit.

Through this, the skin care device 100 according to one embodiment of the present invention may be changed to the first operation mode, the second operation mode, the third operation mode and the fourth operation mode according to the number of times the button 152 is pressed.

However, the button unit 150 is not limited thereto, and the button unit 150 may include a plurality of buttons matched one-to-one with the first operation mode, the second operation mode, the third operation mode and the fourth operation mode.

Moreover, the skin care device 100 according to one embodiment of the present invention may be changed to various operation modes such as an on mode, an off mode and a standby mode in addition to changing to the first operation mode, the second operation mode, the third operation mode and the fourth operation mode described above through the manipulation of the button 152.

The control unit may control the overall operation of the skin care device 100 such as changing an operation mode of the device, supplying/blocking electric power and the like.

Such a control unit may include a main circuit board 182 disposed inside the body 110 and a chipset 184 mounted on one surface of the main circuit board 182, and the chipset 184 may be a controller such as an MCU or AP. In addition, the control unit may include various program codes for controlling various operation modes.

For example, the control unit may store a lookup table that may adjust the wavelength band of light beams output from the light source 142 according to the operation mode or appropriately adjust the magnitude of the DC current applied to the user's skin through the two contact terminals 120a and 120b.

In this case, based on first information on whether the two contact terminals 120a and 120b contact the user's skin and second information on the distance between the light source 142 and the skin, the control unit may automatically control turning on and off the light source 142.

Herein, the first information may be obtained through a voltage drop caused by the user's skin resistance at the two contact terminals 120a and 120b, and the second information may be obtained through a proximity sensor 146.

To this end, as illustrated in FIG. 2, the skin care device 100 according to one embodiment of the present invention may include at least one proximity sensor 146, and the at least one proximity sensor 146 may be mounted on one surface of the circuit board 144 on which the plurality of light sources 142 are mounted.

Accordingly, the at least one proximity sensor 146 may be disposed at a position corresponding to the light-transmitting member 113 similar to the plurality of light sources 142, and when the first surface moves towards the user's skin, the at least one proximity sensor 146 may measure the distance to the user's skin through the light-transmitting member 113.

In this case, the proximity sensor 146 may be mounted on the circuit board 144 to be located at a position relatively closer to the two sensing terminals 130a and 130b than the plurality of light sources 142.

In addition, in a case in which the first surface is formed as an inclined surface and the circuit board 144 is disposed to be inclined at the same inclination as the inclined surface as described above, the proximity sensor 146 may be mounted to be located on the upper end side of the circuit board 144 which is inclined at the same inclination as the inclined surface.

Accordingly, when the skin care device 100 is operated, even if only a partial area of the first surface of the total area of the first skin contacting surface 121 disposed along the first surface comes into contact with the user's skin, the proximity sensor 146 may accurately measure the distance between the plurality of light sources 142 and the user's skin on which treatment is performed.

Through this, when the skin care device 100 according to one embodiment of the present invention is initially operated based on the first information and the second information, the light source 142 may be turned on for the first time only in a state in which the first surface is moved to a position where the user wants to be finally treated.

Moreover, the skin care device 100 according to one embodiment of the present invention may prevent malfunction of the light source 142 based on the first information and the second information, after the initial operation when the light source 142 is turned on for the first time until the care operation is completed, and it is possible to prevent unnecessary interruption of the operation of the light source 142 during the operation of the light source 142.

For example, the control unit may initially turn on the light source 142 during the initial operation, only when both of a state in which the two contact terminals 120a and 120b are in contact with the user's skin and a state in which the distance between the light source 142 and the skin is within a preset range are satisfied on based on the first information and the second information.

In addition, the control unit may control the operation of the light source 142 based on the second information during the skin care operation using the plurality of light sources 142 and the two contact terminals 120a and 120b after the initial operation in which the light source 142 is turned on for the first time.

That is, when the distance between the light source 142 and the skin is within a preset range during the skin care operation, the light source 142 may be kept lit through the control unit, and when the distance between the light source 142 and the skin is more than a preset range, the light source 142 may be turned off through the control unit.

This is to enable the light source 142 to stably operate by controlling the lighting of the light source 142 by the control unit based on the second information obtained through the proximity sensor 146, even if the first information generated through the two contact terminals 120a and 120b is inaccurate because cosmetics applied to the users skin during skin care operation are get on the two contact terminals 120a and 120b.

Moreover, the control unit may maintain the lighting of the light source 142 if the two contact terminals 120a and 120b are at a very close distance to the user's skin in a state in which the two contact terminals 120a and 120b are not in contact with the users skin during the skin care operation using the plurality of light sources 142 and the two contact terminals 120a and 120b after the initial operation in which the light source 142 is turned on for the first time.

Through this, in the process of rubbing the cosmetics applied to the users skin by bringing the first surface into contact with the users skin, even if the two contact terminals 120a and 120b are spaced apart from the users skin at a short distance, the skin care device 100 according to one embodiment of the present invention may prevent unnecessary interruption of the skin care operation by continuously turning on the light source 142.

For this reason, the skin care device 100 according to one embodiment of the present invention may prevent unnecessary interruption of the care operation in advance even if it treats a body part with severe curvature such as the face, thereby achieving a stable skin care operation.

Meanwhile, the skin care device 100 according to one embodiment of the present invention may automatically select the operation method by the control unit based on information on the oil and moisture of the user's skin measured by the two sensing terminals 130a and 130b, and the skin care device 100 may be operated in the operation mode selected through the control unit.

For example, when electric power is supplied through the manipulation of the button 152, the skin care device 100 according to one embodiment of the present invention may be changed to a standby mode to measure oil and moisture of the user's skin through the control unit.

In this state, when the two sensing terminals 130a and 130b come into contact with the skin to be treated, the control unit may obtain information on the oil and moisture of the user's skin through the two sensing terminals 130a and 130b, and then may change the operation mode to a standby mode after diagnosing the current condition of the user's measured skin.

In addition, the control unit may output a result suitable for the current condition of the diagnosed user's skin through the indicator LEDs 149, and the control unit may select an operation mode suitable for the current condition of the user's measured skin.

Herein, the operation mode selected by the control unit may be any one operation mode of the first operation mode, the second operation mode, the third operation mode and the fourth operation mode described above, and in the first operation mode, the second operation mode and the third operation mode, at least one of the wavelength bands of light beams emitted through the plurality of light sources 142 and the intensities of current applied towards the skin through the two contact terminals 120a and 120b may be different from each other.

Preferably, in the first operation mode, the second operation mode and the third operation mode, the wavelength bands of light beams emitted through the plurality of light sources 142 and the intensities of current applied towards the skin through the two contact terminals 120a and 120b may all be different.

Afterwards, when the two contact terminals 120a and 120b come into contact with the skin to be treated, the control unit may operate the skin care device 100 in the selected operation mode.

As described above, the skin care device 100 according to one embodiment of the present invention may allow the user to manually select various operation modes, and also, it may improve the user's convenience by diagnosing the current condition of the user's skin through the control unit and automatically operating in an operation mode suitable for the current condition of the user's diagnosed skin.

Figure 8:
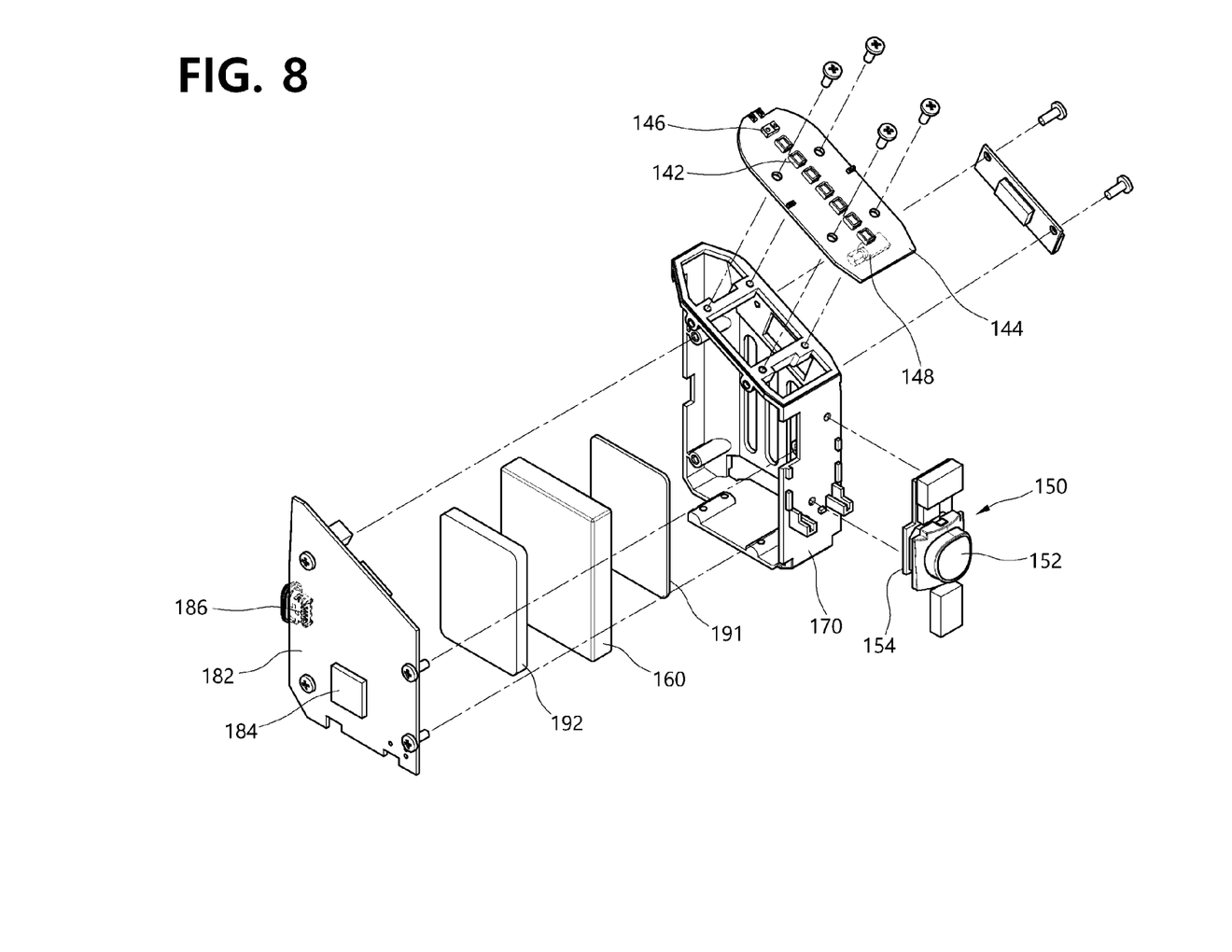
FIG. 8 is an exploded view of FIG. 7.

Meanwhile, the skin care device 100 according to one embodiment of the present invention may include a frame unit 170 inserted into the body 110. As illustrated in FIGS. 7 and 8, such a frame unit 170 may mutually fasten various parts built into the body 110 and may be fixed such that the various parts are disposed at appropriate positions.

For example, the circuit board 144 on which the plurality of light sources 142 are mounted may be detachably coupled to the upper side of the frame unit 170. In addition, based on (b) of FIG. 7, the main circuit board 182 may be detachably coupled to the front part of the frame unit 170, and the button unit 150 may be detachably coupled to the right side of the frame unit 170. In addition, as illustrated in (a) of FIG. 7, the indicator LEDs 149 may be coupled to be located on the opposite side of a surface of the frame unit 170 to which the main circuit board 182 is coupled.

In this case, as illustrated in FIG. 8, the battery 160 for supplying electric power may be disposed inside the frame unit 170, and cushion members 191 and 192 having a predetermined area may be disposed on both surfaces of the battery 160.

Herein, the cushion members 191 and 192 may prevent the flow of the battery 160 disposed inside the frame unit 170 and protect the battery 160 by absorbing an external shock.

Accordingly, by inserting the frame unit 170 to which the circuit board 144 on which the plurality of light sources 142 are mounted, the main circuit board 182, the button unit 150, the indicator LEDs 149, the battery 160 and the like are all fastened into the case 111 and fixing the lower side of the frame unit 170 to the lower case 111b, all assembly may be completed.

Through this, the plurality of light sources 142 and the proximity sensor 146 mounted on the circuit board 144 may be disposed in an area corresponding to the light-transmitting member 113, and the two contact terminals 120a and 120b and the two sensing terminals 130a and 130b may be in one-to-one contact with the plurality of elastic terminals 124 and 134 mounted on the circuit board 144.

For this reason, the two contact terminals 120a and 120b and the two sensing terminals 130a and 130b may be energized with the circuit board 144 via the plurality of elastic terminals 124 and 134.

Meanwhile, the light-transmitting member 113 may protect the user's eyes from light beams emitted to the outside when the light source 142 is turned on. In addition, the light-transmitting member 113 may increase the diffusivity of light beams generated from the light source 142 such that uniform light may be emitted to the outside.

To this end, the light-transmitting member 113 may be provided to have a predetermined transmittance so as to reduce the intensity of light emitted from the light source 142 to the outside, and it may include a component that diffuses light so as to emit uniform light to the outside.

For example, the light-transmitting member 113 may have a transmittance of 70 to 90%, and preferably, a light diffusion PC having a transmittance of 70 to 90% may be used. Herein, the transmittance of the light-transmitting member 113 is exemplified as 70 to 90%, but the present invention is not limited thereto, and as long as the light diffusion property may be increased while protecting the user's eyes, the transmittance of the light-transmitting member 113 may be appropriately adjusted. In addition, the light-transmitting member 113 may be glass.

Meanwhile, the skin care device 100 according to one embodiment of the present invention may further include a notification unit linked to the manipulation of the button 152. When the user manipulates the button 152, the notification unit may provide a notification that the user may easily recognize.

For example, as illustrated in FIG. 8, the notification unit may be a vibration means 148 electrically connected to the circuit board 144, or it may be a sound output means (not illustrated) such as a speaker that outputs sound to the outside. Herein, the vibration means 148 may be a vibration motor or a vibration sensor.

That is, when the user presses the button 152, the control unit may recognize the manipulation of the button 152 and may operate the notification unit to generate vibration for a certain period of time through the vibration means 148 or to output a sound to the outside.

Accordingly, the user may easily recognize the on/off of electric power and change of the operation mode through the manipulation of the button 152, thereby easily identifying the current operating state of the skin care device 100.

Herein, the output pattern of the notification unit may be output in a different pattern for each mode. For example, when the output pattern of the notification unit is a vibration pattern generated by the vibration means 148, the vibration pattern may be output as a pattern in which at least one of the intensity of vibration and the duration of the vibration is different when selecting and changing the first operation mode, the second operation mode and the third operation mode.

In addition, the skin care device 100 according to one embodiment of the present invention may further include a charging terminal 186 for recharging the electric power of the battery 160. For example, as illustrated in FIG. 8, the charging terminal 186 may be mounted on the main circuit board 182.

As such, the charging terminal 186 may be connected to an external power source through a known charging cable.

Through this, the skin care device 100 according to one embodiment of the present invention may recharge the battery 160 using electric power supplied from the outside by receiving electric power from the outside through the charging terminal 186.

Although the embodiments of the present invention have been described, the spirit of the present invention is not limited to the embodiments presented in the present specification. Those skilled in the art who understand the spirit of the present invention could easily propose other embodiments by modifying, changing, deleting or adding components within the same scope of the spirit. Further, these other embodiments also belong to the scope of the spirit of the present invention.

The invention claimed is:

1. A skin care device, comprising: a body including a first surface having a predetermined area; two contact terminals disposed to be spaced apart from each other on the first surface, wherein the two contact terminals are configured to generate a potential difference on a user's skin to change an electrical environment of the user's skin when electric power is applied; two sensing terminals disposed to be spaced apart from each other on the first surface, wherein the two sensing terminals are configured to sense oil and moisture on the user's skin when the electric power is applied; a plurality of light sources mounted on a circuit board disposed inside the body, the circuit board being located behind the first surface, wherein the plurality of the light sources are configured to emit light beams having different wavelength bands; and a control unit for controlling an operation of the skin care device, wherein each of the two contact terminals includes a first skin contact surface that protrudes from the first surface at a predetermined height; and wherein each of the two sensing terminals includes: a second skin contact surface protruding from the first surface at a predetermined height; an extension part that extends a predetermined length downward from an edge of the second skin contact surface and is fixed to the body; and a terminal contact surface bent in one direction from an end of the extension portion, wherein the terminal contact surface is in contact with an elastic terminal mounted on the circuit board and is electrically connected to the circuit board.

2. The skin care device of claim 1, wherein the two contact terminals and the two sensing terminals are disposed in an annular shape along the periphery of an edge side of the first surface, and the two sensing terminals are disposed to be located between the two contact terminals.

3. The skin care device of claim 1, wherein the first surface has an inclined surface having a predetermined inclination, and the first surface is an upper surface of the body.

4. The skin care device of claim 3, wherein the two sensing terminals are disposed to be located on an upper end side of the inclined surface.

5. The skin care device of claim 1, wherein the second skin contact surface of the each of the two sensing terminals in contact with the user's skin has a narrower area than the first skin contact surface of the each of the contact terminals in contact with the user's skin.

6. The skin care device of claim 1, wherein the skin care device further comprises a proximity sensor mounted on the circuit board.

7. The skin care device of claim 6, wherein the proximity sensor is disposed to be located at a position relatively closer to the two sensing terminals than the plurality of light sources.

8. The skin care device of claim 6, wherein the control unit is configured to change the plurality of the light sources to a light-off state, when the two contact terminals are not in contact with the user's skin in a state in which the plurality of the light sources are turned on, and a spacing distance from the user's skin measured through the proximity sensor is more than a preset distance, and wherein the control unit is configured to maintain a light-on state of the plurality of the light sources, when the two contact terminals are not in contact with the user's skin in a state in which the plurality of the light sources are turned on, and the spacing distance from the user's skin measured through the proximity sensor is within a preset distance.

9. The skin care device of claim 1, wherein the two contact terminals are in contact with a plurality of elastic terminals mounted on the circuit board to be electrically connected to the circuit board.

10. The skin care device of claim 1, wherein the skin care device further comprises a plurality of indicator LEDs embedded on the body to emit light beams according to user's oil and moisture condition information measured through the two sensing terminals.

11. The skin care device of claim 1, wherein the body has a relatively wider width from top to bottom.

12. The skin care device of claim 1, wherein the body comprises a case having an inner space with an open upper part and an annular connecting member integrally formed on an open upper edge side of the case, and the two contact terminals and the two sensing terminals are integrally formed with the annular connecting member.

13. The skin care device of claim 12, wherein the body comprises a light-transmitting member integrally formed inside the annular connecting member so as to emit light beams generated by the plurality of light sources to an outside.

* * * * *